United States Patent [19]

Minderhoud et al.

[11] Patent Number: 4,594,468

[45] Date of Patent: Jun. 10, 1986

[54] PROCESS FOR THE PREPARATION OF MIDDLE DISTILLATES FROM SYNGAS

[75] Inventors: Johannes K. Minderhoud; Swan T. Sie, both of Amsterdam, Netherlands

[73] Assignee: Shell Oil Company, Houston, Tex.

[21] Appl. No.: 780,722

[22] Filed: Sep. 27, 1985

Related U.S. Application Data

[63] Continuation of Ser. No. 646,193, Aug. 31, 1984, abandoned.

[30] Foreign Application Priority Data

Sep. 12, 1983 [NL] Netherlands ............................ 8303142

[51] Int. Cl.$^4$ .............................................. C10G 51/02
[52] U.S. Cl. ...................... 585/310; 208/950; 208/110; 518/715
[58] Field of Search ..................... 208/950, 110, 49; 518/715; 585/310

[56] References Cited

U.S. PATENT DOCUMENTS

| 2,516,699 | 7/1950 | Hemminger | 208/950 |
|---|---|---|---|
| 3,932,552 | 1/1976 | Starks | 208/950 |
| 4,032,556 | 6/1977 | Banks | 518/715 |
| 4,046,830 | 9/1977 | Kuo | 585/310 |
| 4,252,736 | 2/1981 | Haag et al. | 585/310 |
| 4,279,830 | 7/1981 | Haag et al. | 208/950 |
| 4,385,193 | 5/1983 | Bijwaard et al. | 585/310 |
| 4,423,156 | 12/1983 | Büssemeier | 518/715 |
| 4,471,145 | 9/1984 | Chu et al. | 208/950 |

FOREIGN PATENT DOCUMENTS

2536488  12/1976  Fed. Rep. of Germany ...... 518/715

*Primary Examiner*—John Doll
*Assistant Examiner*—Lance Johnson

[57] ABSTRACT

Middle distillates are prepared from syngas by a two-stage series-flow process comprising (1) Fischer-Tropsch synthesis over a special Zr, Ti or Cr promoted Co-catalyst followed by (2) hydroconversion of the total synthesized product over a supported noble metal catalyst.

21 Claims, No Drawings

PROCESS FOR THE PREPARATION OF MIDDLE DISTILLATES FROM SYNGAS

This is a continuation of application Ser. No. 646,193 filed Aug. 31, 1984, now abandoned.

BACKGROUND OF THE INVENTION

The invention relates to a process for the preparation of middle distillates from a mixture of carbon monoxide and hydrogen.

The preparation of hydrocarbons from a $H_2/CO$ mixture by contacting said mixture at elevated temperature and pressure with a catalyst is known in the literature as the Fischer-Tropsch hydrocarbon synthesis process. Catalysts frequently used for this purpose contain one or more metals of the iron group together with one or more promoters and a carrier material. The products that can be prepared by using these catalysts usually have a very broad molecular weight distribution and in addition to branched and unbranched paraffins, they often contain considerable quantities of olefins and oxygen-containing organic compounds. Often only a minor portion of the products obtained consists of middle distillates. Not only the yield of the gas oil obtained, but owing to the presence of the afore-mentioned olefins and oxygen-containing organic compounds, its cetane number is unsatisfactory, as well. Consequently the direct conversion of $H_2/CO$ mixtures according to the Fischer-Tropsch process is rather an unattractive route for the preparation of middle distillates on a technical scale.

In the present patent application the term "middle distillates" is used to designate hydrocarbon mixtures whose boiling range corresponds substantially with that of the kerosene and gas oil fractions obtained in the conventional atmospheric distillation of crude mineral oil. The middle distillate range lies mainly between approximately 150° and 360° C., with the fractions boiling between about 200° and 360° C. usually being referred to as gas oil.

Discovery was recently made of a class of Fischer-Tropsch catalysts which have the property of yielding a product in which only very small quantities of olefins and oxygen-containing organic compounds occur and which consists almost entirely of unbranched paraffins, which paraffins boil to a considerable extent above the middle distillate range. Owing to the high normal paraffins/isoparaffins ratio and the low contents of olefins and oxygen-containing organic compounds of this product, the gas oil present therein has a very high cetane number. It has been found that the high-boiling part of this product can be converted in high yield into middle distillates by hydrocracking. The feed chosen to be hydrocracked is at least the part of the product whose initial boiling point lies above the final boiling point of the heaviest middle distillate desired as final product. The hydrocracking, which is characterized by a very low hydrogen consumption, yields a product in which, owing to the high normal paraffins/isoparaffins ratio, the gas oil has a very high cetane number. The cetane number is one of the most important quality criteria for a gas oil when it is to be used as fuel for diesel engines. The gas oils used for this purpose are generally composed by mixing gas oils having a high cetane number with gas oils having a low cetane number. In view of the ample availability of gas oils having a low cetane number—such as cycle oils obtained as by-product in catalytic cracking—and the limited availability of gas oils having a high cetane number, there is an urgent need for the latter gas oils. According as a gas oil has a higher cetane number it will be a more valuable mixing component for the preparation of diesel fuels, since such a gas oil enables larger amounts of inferior gas oil to be taken up in the mixture and nevertheless enables the cetane number required in actual practice to be attained. In view of the fact that the above-mentioned two-step process offers the opportunity of preparing gas oils having a cetane number higher than 70, while the gas oils that are used as diesel fuel should have a cetane number of 40–50, it will be clear that the two-step process is excellently suitable for the preparation of valuable mixing components for diesel fuels.

The Fischer-Tropsch catalysts used in the first step of the two-step process contain silica, alumina or silica-alumina as carrier material, and cobalt together with zirconium, titanium and/or chromium as catalytically active metals in such quantities that the catalysts contain 3–60 pbw cobalt and 0.1–100 pbw zirconium, titanium and/or chromium per 100 pbw carrier material. The catalysts are prepared by deposition of the appropriate metals onto the carrier material by kneading and/or impregnation. For further information on the preparation of these catalysts by kneading and/or impregnation reference may be made to Netherlands patent application No. 8301922, recently filed in the name of the Applicant, in which there is also given a description of the above-mentioned two-step process for the preparation of middle distillates from $H_2/CO$ mixtures.

Until recently, the two-step process was carried out as follows. The $H_2/CO$ mixture used as feed was contacted in the first step at a pressure of 20–30 bar with the cobalt catalyst. Subsequently, the reaction product was separated at atmospheric pressure into two fractions, viz. a $C_5^+$ fraction and a fraction comprising the remaining reaction components, viz. $C_4^-$ hydrocarbons, water, carbon dioxide and unconverted carbon monoxide and hydrogen. Finally the $C_5^+$ fraction, together with added hydrogen, was contacted in the second step at a pressure of about 130 bar with a catalyst containing one or more noble metals of Group VIII supported on a carrier. As regards this embodiment of the two-step process the following may be observed.

Although in the preparation of middle distillates according to the two-step process the part of the product of the first step whose initial boiling point lies above the final boiling point of the heaviest middle distillate desired as end product will suffice as feed for the second step, thus far the total $C_5^+$ fraction of the product of the first step was used for the purpose, since under the influence of the catalytic hydrotreatment the quality of the gasoline, influence of the catalytic hydrotreatment the quality of the gasoline, kerosene and gas oil fractions therein had been found to improve.

The high pressure used in the second step was thus far thought to be necessary on account of disappointing results obtained when carrying out the second step at a lower pressure. This may be seen from the following experimental results obtained in working up the product prepared by Experiment 13 of Netherlands patent application No. 8301922, also filed as U.S. counterpart application, Ser. No. 594618, filed Mar. 29, 1984, now U.S. Pat. No. 4,522,939, issued June 11, 1985 which is incorporated herein by reference. Contacting the $C_5^+$ fraction of this product together with hydrogen at a temperature of 300° C. and a pressure of 130 bar with the Pt/SiO$_2$—Al$_2$O$_3$ catalyst used in Experiment 20 of said patent application led to a product whose 200°-360° C. fraction had a high normal paraffins/isoparaffins ratio. A repeat of this experiment at a pressure of 20 bar and otherwise similar conditions produced a decrease in the yield of 200°-360° C. fraction as well as quite a sharp fall in the normal paraffins/isoparaffins ratio of this fraction. The latter phenomenon in particular is highly undesirable in view of the accompanying decrease in cetane number. In order to raise the yield of 200°-360° C. fraction, Experiment 20 was repeated at 20 bar, but using a lower space velocity. It is true that in this way there could be achieved a yield of 200°-360° C. fraction corresponding with that obtained in the experiment using 130 bar, but it led to yet a further decrease in the normal paraffins/isoparaffins ratio of the fraction.

As remarked hereinbefore, the two-step process was thus far carried out by separation at atmospheric pressure of the C$_5$+ fraction from the product of the first step prepared at a pressure of 20-30 bar, and processing of said fraction together with hydrogen in the second step a about 130 bar. The assumption that by the choice of the H$_2$/CO molar ratio of the feed for the first step and the reaction conditions of the first step the quantity of hydrogen present in the product of the second step can be so regulated that this product contains sufficient hydrogen to carry out the hydrocracking in the second step led to the question whether it might be possible to carry out the present two-step process in "series-flow", which would considerably bring down the cost involved in the process. As already known, carrying out a two-step process in "series-flow" involves using the entire reaction product of the first step—without components being removed therefrom or components being added thereto—as feed for the second step which is carried out at substantially the same pressure as the first step.

Although in view of the cost involved carrying out the present two-step process in "series-flow" is much to be preferred to the procedure adopted thus far, there are two aspects which raise considerable doubt as to its practical possibilities. The first is the pressure. When the process is carried out in "series-flow", the second step should be carried out substantially at the same low pressure as the first step. As seen from experiments conducted earlier, a reduction of the pressure in the second step results in a very severe drop of the normal paraffins/isoparaffins ratio of the gas oil. The second aspect concerns the composition of the feed for the second step. When the process is carried out in "series-flow", the total reaction product of the first step is used as feed for the second step. In this connection it should be taken into account that generally no more than ⅓ of the reaction product of the first step consists of C$_5$+ fraction while the remainder consists of water, C$_1$-C$_4$ hydrocarbons, carbon dioxide and unconverted hydrogen and carbon monoxide. In consequence of the development of the Fischer-Tropsch reaction (CO+2H$_2$→—CH$_2$—+H$_2$O) the reaction product of the first step contains more water than hydrocarbons, expressed by weight. In view of the composition of said product—in particular the large amount of water present therein—it is very doubtful of course whether the noble metal catalyst used in the second step will still be able to bring about the desired conversion.

In spite of the expectations regarding the practical possibilities of the present two-step process in "series-flow", which, on account of the above observations, were bound to be negative, an experimental investigation in that direction was nevertheless carried out. Surprisingly, in this investigation it was not only found that carrying out the two-step process in "series-flow" leads to a yield similar to that obtained in the two-step process carried out in the conventional way, but also that the gas oil produced in "series-flow" has a much higher normal paraffins/isoparaffins ratio. An explanation of this surprising result can possibly be found in the fact that the composition of the feed for the second step is different. In addition to the C$_5$+ fraction and hydrogen which are present in the feed for the second step when the two-step process is conducted in the conventional way, this feed now also contains C$_1$-C$_4$ hydrocarbons, carbon monoxide, carbon dioxide and water. Apparently the presence of one or more of these components in the feed has so favorable an influence on the normal paraffins/isoparaffins ratio as not only to offset the afore-noted adverse effect of pressure reduction on the normal paraffins/isoparaffins ratio of the gas oil, but even to enhance this ratio considerably.

SUMMARY OF THE INVENTION

The present patent application therefore relates to a process for the preparation of middle distillates from a mixture of carbon monoxide and hydrogen, in which a H$_2$ and CO containing feed is contacted in the first step at elevated temperature and pressure with a catalyst containing 3-60 pbw cobalt and 0.1-100 pbw of at least one other metal chosen from the group formed by zirconium, titanium and chromium per 100 pbw silicate, alumina or silica-alumina, which catalyst has been prepared by kneading and/or impregnation, in which in a second step the complete reaction product of the first step is subjected to a hydrocracking treatment by contacting it at an elevated temperature and a pressure which corresponds substantially with that used in the first step, with a catalyst containing one or more noble metals of Group VIII supported on a carrier, and in which the H$_2$/CO molar ratio of the feed and the reaction conditions of the first step are so chosen that the reaction product of the first step contains sufficient unconverted hydrogen for carrying out the hydrocracking reaction in the second step.

In the process of the invention it is preferred to use in the first step the cobalt catalysts which form the subject matter of Netherlands patent application No. 8301922. These are catalysts which satisfy the relation $$(3 + 4R) > \frac{L}{S} > (0.3 + 0.4 R),$$

L = the total quantity of cobalt present on the catalyst, expressed as mg Co/ml catalyst,
S = the surface area of the catalyst, expressed as m$^2$/ml catalyst, and
R = the weight ratio of the quantity of cobalt deposited on the catalyst by kneading to the total quantity of cobalt present on the catalyst.

DETAILED DESCRIPTION OF THE INVENTION

The preparation of the cobalt catalysts which are used in the first step of the process of the invention is preferably carried out according to one of the three procedures mentioned hereinafter:

(a) first cobalt is deposited in one or more steps by impregnation and subsequently the other metal is deposited in one or more steps, also by impregnation,
(b) first the other metal is deposited in one or more steps by impregnation and subsequently the cobalt is deposited in one or more steps, also by impregnation, and
(c) first cobalt is deposited in one or more steps by kneading and subsequently the other metal is deposited in one or more steps by impregnation.

In the process according to the invention preference is given to the use of cobalt catalysts containing 15–50 pbw cobalt per 100 pbw carrier. The preferred quantity of other metal present in the cobalt catalysts depends on the way in which this metal has been deposited. In the case of catalysts where first cobalt has been deposited on the carrier, followed by the other metal, preference is given to catalysts containing 0.1–5 pbw other metal per 100 pbw carrier. In the case of catalysts where first the other metal has been deposited on the carrier, followed by the cobalt, preference is given to catalysts containing 5–40 pbw of the other metal per 100 pbw carrier. Preference is given to zirconium as the other metal and to silica as carrier material. In order to be suitable for use the cobalt catalysts should first be reduced. This reduction may suitably be carried out by contacting the catalyst at a temperature between 200° and 350° C. with a hydrogen-containing gas.

In the process according to the invention, in the second step a catalyst is used which preferably contains 0.1–2%w, and in particular 0.2–1%w, of one or more noble metals of Group VIII supported on a carrier. Preference is given to catalysts containing platinum or palladium as noble metal. Examples of suitable carriers for the noble metal catalysts are amorphous oxides of the elements of Groups II, III and IV, such as silica, alumina, magnesia and zirconia and also mixtures of these oxides, such as silica-alumina, silica-magnesia and silica-zirconia. Preferred carriers for the noble metal catalysts are silica-aluminas.

In the process of the invention the first step is preferably carried out at a temperature of 125°–350° C. and in particular of 175°–275° C. and the second step is preferably carried out at a temperature of 200°–400° C. and in particular of 250°–350° C. The process is preferably carried out at a pressure of 5–100 bar and in particular of 10–75 bar.

$H_2/CO$ mixtures which are eligible to be used for the preparation of middle distillates according to the invention can very suitably be obtained, starting from a heavy carbonaceous material such as coal, or starting from light hydrocarbons such as natural gas, by steam reforming or partial oxidation. In the process according to the invention the $H_2/CO$ molar ratio of the feed and the choice of the reaction conditions in the first step should be so chosen that the reaction product of the first step contains sufficient unconverted hydrogen for carrying out the hydrocracking reaction in the second step. Since the $H_2/CO$ consumption ratio of the present cobalt catalysts is about 2, in the process according to the invention, in those cases where the highest possible CO conversion is aimed at, it is preferred to use $H_2/CO$ mixtures having a $H_2/CO$ molar ratio higher than 2. Very suitable for carrying out the present process is a feed which can be obtained in the steam reforming of natural gas, which yields $H_2/CO$ mixtures having a $H_2/CO$ molar ratio of about 3, as is well-known. If the feed for the first step of the process of the invention available is a $H_2/CO$ molar ratio having a $H_2/CO$ molar ratio of 2 or less, then the $H_2/CO$ molar ratio of said feed can be increased preparatory to contacting the feed with the cobalt catalysts. Such an increase of the $H_2/CO$ molar ratio may be brought about by, inter alia, addition of hydrogen, removal of carbon monoxide, mixing with a hydrogen-rich $H_2/CO$ mixture or by subjecting the low-hydrogen feed to the CO-shift reaction. Optionally the CO-shift reaction can be carried out in situ by addition in the first step of the process of a physical mixture of CO-shift catalyst and the cobalt catalyst. It is also possible to subject low-hydrogen synthesis gases to the process according to the invention without raising their $H_2/CO$ molar ratios. The reaction conditions chosen in the first step should then be sufficiently mild for only part of the hydrogen available to participate in the Fischer-Tropsch reaction. Naturally this cannot be achieved without some sacrifice in yield of hydrocarbons.

Besides as an individual two-step process for the preparation of middle distillates from $H_2/CO$ mixtures which have been prepared from, for instance, coal, heavy mineral oil fractions or natural gas, the process of the invention can also very suitably be used as part of a three-step process for the conversion of said $H_2/CO$ mixtures. In the latter case the $H_2/CO$ mixture available as feed is in the first step partially converted into substantially aliphatic hydrocarbons, aromatic hydrocarbons or oxygen-containing organic compounds, and subsequently unconverted hydrogen and carbon monoxide, together with other components from the product of the first step if desired, are used as feed for the process according to the invention.

The invention is now illustrated with the aid of the following example.

EXAMPLE

Two $Co/Zr/SiO_2$ catalysts (Catalysts 1 and 2) were prepared by impregnation of a silica carrier with solutions of cobalt and zirconium compounds. In each impregnation step there was used a quantity of solution whose volume correspond substantially with the pore volume of the carrier. After each impregnation step the solvent was removed by heating and the material was calcined at 500° C. Catalysts 1 and 2 were prepared as follows.

Catalyst 1

(=Catalyst 9 of Netherlands patent application 8301922)

One-step impregnation of a silica carrier with a solution of cobalt nitrate in water, followed by one-step impregnation of the cobalt-loaded carrier with a solution of zirconium nitrate in water. Catalyst 1 comprised 25 pbw cobalt and 0.9 pbw zirconium per 100 pbw silica. For Catalyst 1 L was 98 mg/ml and S was 96 m$^2$/ml and consequently L/S was 1.02 mg/m$^2$.

Catalyst 2

(=Catalyst 2 of Netherlands patent application 8301922)

Three-step impregnation of a silica carrier with a solution of zirconium tetra-n-propoxide in a mixture of n-propanol and benzene, followed by one-step impregnation of the zirconium-loaded carrier with a solution of cobalt nitrate in water. Catalyst 2 comprised 25 pbw cobalt and 18 pbw zirconium per 100 pbw silica. For catalyst 2 L was 97 mg/ml and S was 100 m$^2$/g and consequently L/S was 0.97 mg/m$^2$.

Catalyst 3

(=catalyst used in Experiment 20 of Netherlands patent application 8301922).

Pt/SiO$_2$—Al$_2$O$_3$ catalyst comprising 0.82 pbw platinum per 100 pbw carrier, 14.6%w of the carrier consisting of alumina and 85.4%w of silica.

Catalyst 4

Pd/SiO$_2$—Al$_2$O$_3$ catalyst comprising 0.3 pbw palladium per 100 pbw carrier, 41%w of the carrier consisting of alumina and 59%w of silica.

Hydrocarbon synthesis

Catalysts 1-4 were used in nine experiments (Experiments 1-9) in the preparation of hydrocarbons from mixtures of carbon monoxide and hydrogen. Before being used Catalysts 1 and 2 were reduced at 250° C. in a hydrogen-containing gas.

EXPERIMENT 1

(=Experiment 13 of Netherlands patent application 8301922)

In this experiment a H$_2$/CO mixture having a H$_2$/CO molar ratio of 2 was contacted at a temperature of 220° C. and a pressure of 20 bar with Catalyst 1. The composition of the reaction product obtained is given in Table 1.

EXPERIMENTS 2-4

In these experiments the C$_5$+ fraction of the reaction product obtained by Experiment 1 was contacted at 300° C. and at various pressures and space velocities with Catalyst 3. The conditions used in these experiments and the results obtained are given in Table II.

EXPERIMENT 5

In this experiment a H$_2$/CO mixture having a H$_2$/CO molar ratio 3 was contacted at a temperature of 204° C. and a pressure of 20 bar with Catalyst 2. The composition of the reaction product obtained is given in Table I.

EXPERIMENTS 6 AND 7

In these experiments the C$_5$+ fraction of the reaction product obtained by Experiment 5 was contacted at 300° C. and at various pressures and space velocities with Catalyst 3. The conditions used in these experiments and the results obtained are given in Table II.

EXPERIMENT 8

In this experiment a H$_2$/CO mixture having a H$_2$/CO molar ratio 3 was contacted in the first step at 204° C. and a pressure of 20 bar with Catalyst 2, and subsequently the total reaction product of the first step was contacted in a second step at a temperature of 300° C. and a pressure of 20 bar with Catalyst 3. The C$_5$+ fraction of the product of the second step contained 44%w gas oil boiling between 200° and 360° C., which gas oil had a normal paraffins/isoparaffins ratio of 10.5.

EXPERIMENT 9

This experiment was carried out substantially in the same manner as Experiment 8, the differences being:
(a) temperature in the first step: 225° C.,
(b) temperature in the second step: 320° C., and
(c) catalyst in the second step: Catalyst 4.

The C$_5$+ fraction of the product of the second step comprised 43%w gas oil boiling between 200° and 360° C., which gas oil had a normal paraffins/isoparaffins ratio of 9.2.

Of Experiments 1-9 only Experiments 8 and 9 are experiments according to the invention. These experiments, which were carried out in "series-flow", yielded a gas oil having a very high normal paraffins/isoparaffins ratio. Experiments 1-7 fall outside the scope of the invention. They have been included in the patent application for comparison.

Experiment 1 combined with Experiment 2, and Experiment 5 combined with Experiment 6, show the two-step process as carried out in the conventional manner, starting from H$_2$/CO mixtures having H$_2$/CO molar ratios of 2 and 3, respectively. In both cases the gas oils obtained have high normal paraffins/isoparaffins ratios (6.1 and 6.4, respectively).

Comparison of the results of Experiments 2-4 and comparison of the results of Experiments 6 and 7 show the adverse effect of lowering the pressure in the second step. Reduction of the pressure from 130 to 20 bar at an unchanged yield of gas oil leads to a sharp fall in the normal paraffins/isoparaffins ratio of the gas oil (from 6.1 to 2.3 and from 6.4 to 2.5, respectively).

TABLE I

|  | Exp. 1 | Exp. 5 |
|---|---|---|
| Composition of the total reaction product prepared by Experiment No., expressed in g. |  |  |
| C$_5$+ | 100 | 100 |
| C$_1$-C$_4$ | 20 | 31 |
| H$_2$ | 4 | 20 |
| CO | 42 | 19 |
| CO$_2$ | 4 | 2 |
| H$_2$O | 149 | 165 |
| Gasoil content (200-360° C.) of C$_5$+ fraction, % w | 30 | 31 |

TABLE II

|  | Experiment No. | | | | |
|---|---|---|---|---|---|
|  | 2 | 3 | 4 | 6 | 7 |
| Temperature, °C. | 300 | 300 | 300 | 300 | 300 |
| Pressure, bar | 130 | 20 | 20 | 130 | 20 |
| Space velocity, g.g$^{-1}$.h$^{-1}$ | 1.2 | 1.2 | 0.6 | 1.2 | 0.6 |
| Yield of gas oil (200-360° C.), % w on feed | 46 | 40 | 46 | 44 | 44 |
| Normal paraffins/isoparaffins ratio of gas oil | 6.1 | 2.7 | 2.3 | 6.4 | 2.5 |

What is claimed is:

1. A process for the preparation of middle distillates from a mixture of carbon monoxide and hydrogen, characterized in that a H$_2$ and CO containing feed is contacted in the first step at elevated temperature and pressure with a catalyst comprising 3-60 pbw cobalt and 0.1-100 pbw of at least one other metal chosen from the group formed by zirconium, titanium and chromium per 100 pbw silica, alumina or silica-alumina, which catalyst has been prepared by kneading and/or impregnation and satisfies the relation $$(3 + 4R) > \frac{L}{S} > (0.3 + 0.4 R),$$

wherein

L = the total quantity of cobalt present on the catalyst, expressed as mg Co/ml catalyst, S = the surface area of the catalyst, expressed as m²/ml catalyst, and R = the weight ratio of the quantity of cobalt deposited on the catalyst by kneading to the total quantity of cobalt present on the catalyst, and that in a second step the total reaction product of the first step, without components being removed therefrom or component being added thereto, is subjected to a hydrocracking treatment by contacting it at an elevated temperature and a pressure which corresponds substantially with that used in the first step, with a catalyst comprising one or more noble metals of Group VIII supported on a carrier, the $H_2/CO$ molar ratio of the feed and the reaction conditions of the first step being so chosen that the reaction product of the first step contains sufficient unconverted hydrogen for carrying out the hydrocracking reaction in the second step.

2. A process as claimed in claim 1, characterized in that in the first step a catalyst is used which has been prepared by first depositing cobalt in one or more steps by impregnation and subsequently depositing the other metal in one or more steps, also by impregnation.

3. A process as claimed in claim 1, characterized in that in the first step a catalyst is used which has been prepared by first depositing the other metal in one or more steps by impregnation and subsequently depositing cobalt in one or more steps, also by impregnation.

4. A process as claimed in claim 1, characterized in that in the first step a catalyst is used which has been prepared by first depositing cobalt in one or more steps by kneading and subsequently depositing the other metal in one or more steps by impregnation.

5. A process as claimed in claim 1, characterized in that in the first step a catalyst is used which comprises 15–50 pbw cobalt per 100 pbw carrier.

6. A process as claimed in claim 1, characterized in that in the first step a catalyst is used which has been prepared by depositing first cobalt and subsequently the other metal, and which comprises 0.1–5 pbw of the other metal per 100 pbw carrier.

7. A process as claimed in claim 1, characterized in that in the first step a catalyst is used which has been prepared by depositing first the other metal and subsequently cobalt, and which comprises 5–40 pbw of the other metal per 100 pbw carrier.

8. A process as claimed in claim 1, characterized in that in the first step a catalyst is used which contains zirconium as other metal.

9. A process as claimed in claim 1, characterized in that in the first step a catalyst is used which contains silica as carrier.

10. A process as claimed in claim 1, characterized in that in the first step a catalyst is used which has previously been reduced by contacting at it a temperature between 200° and 350° C. with a hydrogen-containing gas.

11. A process as claimed in claim 1, characterized in that in the second step a catalyst is used which comprises 0.1–2%w of one or more noble metals from Group VIII supported on a carrier.

12. A process as claimed in claim 11, characterized in that in the second step a catalyst is used which comprises 0.2–1%w of one or more noble metals supported on a carrier.

13. A process as claimed in claim 12, characterized in that in the second step a catalyst is used which comprises platinum or palladium as noble metal from Group VIII.

14. A process as claimed in claim 13, characterized in that in the second step a catalyst is used which comprises silica-alumina as carrier.

15. A process as claimed in claim 14, characterized in that the first step is carried out at a temperature of 125°–350° C.

16. A process as claimed in claim 15, characterized in that the first step is carried out at a temperature of 175°–275° C.

17. A process as claimed in claim 16, characterized in that the second step is carried out at a temperature of 200°–400° C.

18. A process as claimed in claim 17, characterized in that the second step is carried out at a temperature of 250°–350° C.

19. A process as claimed in claim 18, characterized in that it is carried out at a pressure of 5–100 bar.

20. A process as claimed in claim 19, characterized in that it is carried out at a pressure of 10–75 bar.

21. A process as claimed in claim 20, characterized in that a feed is used whose $H_2/CO$ molar ratio is higher than 2.

* * * * *